United States Patent [19]

Keates et al.

[11] Patent Number: 4,619,657
[45] Date of Patent: Oct. 28, 1986

[54] FLEXIBLE INTRAOCULAR LENS HOLDER

[76] Inventors: Richard H. Keates, 264 N. Drexel Ave., Columbus, Ohio 43209; Richard T. Schneider, 3550 NW. 33rd Pl., Gainesville, Fla. 32605; Timothy E. Roxey, 2222 NW. 36 Ter., Gainesville, Fla. 32605; John D. Cox, 3416 SE. 29th Blvd., Gainesville, Fla. 32601

[21] Appl. No.: 814,080

[22] Filed: Dec. 23, 1985

Related U.S. Application Data

[63] Continuation of Ser. No. 648,079, Sep. 7, 1984, abandoned.

[51] Int. Cl.⁴ ............................................. A61F 2/16
[52] U.S. Cl. ................................. 623/6; 128/303 R; 206/5.1; 206/45.34
[58] Field of Search ...................... 623/6; 128/303 R; 206/5.1, 45.34, 210

[56] References Cited

U.S. PATENT DOCUMENTS

| | | | |
|---|---|---|---|
| 4,242,760 | 1/1981 | Rainin | 3/13 |
| 4,244,060 | 1/1981 | Hoffer | 3/13 |
| 4,251,887 | 2/1981 | Anis | 3/13 |
| 4,254,510 | 4/1981 | Tennant | 3/13 |
| 4,343,050 | 8/1982 | Kelman | 3/13 |
| 4,373,218 | 2/1983 | Schachar | 623/6 |
| 4,423,809 | 1/1984 | Mazzocco | 206/5.1 |
| 4,424,597 | 1/1984 | Schlegel | 623/6 |
| 4,451,938 | 6/1984 | Kelman | 3/13 |
| 4,573,998 | 3/1986 | Mazzocco | 623/6 |

FOREIGN PATENT DOCUMENTS

| | | | |
|---|---|---|---|
| 2114315 | 8/1983 | United Kingdom | 623/6 |
| 2124500 | 2/1984 | United Kingdom | 623/6 |

Primary Examiner—Ronald L. Frinks
Attorney, Agent, or Firm—Merchant, Gould, Smith, Edell, Welter & Schmidt

[57] ABSTRACT

Flexible holders are disclosed which allow one or more synthetic lenses to be securely positioned within the intraocular chambers of the eye, and which can be inserted into the eye through corneal incisions of minimal size.

29 Claims, 5 Drawing Figures

FLEXIBLE INTRAOCULAR LENS HOLDER

This is a continuation, of application Ser. No. 648,079, filed Sept. 7, 1984, now abandoned.

FIELD OF THE INVENTION

The present invention is directed to flexible holders which allow one or more synthetic lenses to be securely positioned within the intraocular chambers of the human eye, and which can be inserted into the eye through corneal incisions of minimal size.

BACKGROUND OF THE INVENTION

Many different types of synthetic intraocular lens structures have been developed to replace the natural lens of the human eye after lens removal during cataract surgery. During such operations, an opening or incision is made in the cornea and in the anterior surface of the capsular bag, commonly in the area adjacent to the pupilary aperture. The damage lens tissue is then removed by means of a vacuum tool resulting in a total loss of vision to the affected patient. In order to restore normal or correctable vision to the patient, a variety of lens structures have been developed which are designed to be affixed in the intraocular space of the eye. Such structures commonly comprise two portions: a centrally positioned lens and two or more appendages attached to the body of the lens which function to position and secure the lens in front of or just behind the pupil.

The artificial lens is formed from an optically clear substance and shaped so as to focus the impinging light onto the retina of the eye. Such lenses are commonly optically formed so as to be plano-convex, convex-plano or bi-convex. The appendages attached to the lens typically comprise flexible legs or resilient plastic or metal fibers which are designed to make point contact with the appropriate structures in the interior of the eye. One commonly employed type of intraocular lens structure is designed to position the lens in the anterior chamber of the eye just in front of the pupil. Such devices are designed to operate by wedging the flexible lens fibers or loops into the anterior chamber angle. Intraocular lens structures of this type are disclosed, for example, by K. J. Hoffer (U.S. Pat. No. 4,244,060), J. L. Tennant (U.S. Pat. No. 4,254,510), E. A. Rainin (U.S. Pat. No. 4,242,760), and C. D. Kelman (U.S. Pat. No. 4,343,050). Such structures may be inserted via loaded plastic sleeves which are then withdrawn from the eye leaving the lens structure to be positioned by conventional techniques as disclosed by A. Y. Anis in U.S. Pat. No. 4,251,887.

Although such intraocular lens structures have successfully addressed many of the problems associated with the restoration of vision following lens removal operations, their insertion and positioning within the eye presents many difficulties. In the first place, the use of discreet attachment appendages, such as flexible legs and loops, tends to localize contact of the structure with the supporting tissues. Such localized pressure can lead to distortion of the pupil and eye irritation. Furthermore, the support appendages which are attached to the lens body effectively increase the size of the lens and the dimensions of the incision which must be made in the eye in order to insert the structure. Especially in the case of elderly patients, such large incisions lead to increased recovery times and healing problems. Although resilient attachment means, such as those formed of plastic fibers, may be compressed prior to the insertion of the lens structure into the eye via the incision, their decompression, once the structure is within the eye may lead to a whipping action which can tear the iris and cause bleeding and other complications.

Furthermore, the need to minimize the size of the incision in the eye has heretofore resulted in the development of intraocular lens structures which comprise only one lens body. Such structures do not fully address the vision problems of patients who normally require bi- or trifocal-type lenses to correct near-far vision discrepencies.

Thus, a need exists for intraocular lens structures which can be inserted into the eye through minimally sized incisions and can be securely positioned within the eye without placing undue or localized pressure upon the structures of the eye. Furthermore, a need exists for intraocular lens structures which will introduce a plurality of lens bodies into the interior space of the eye while causing minimal trauma thereto.

BRIEF DESCRIPTION OF THE INVENTION

The present invention is directed to an intraocular lens structure which comprises a flexible lens holder incorporating one or more lens bodies. The holder will comprise means adapted to individually secure the artificial lenses to the holder in a coplanar fashion. Preferred means include one or more optically-transparent lens pockets which are formed within or attached to the body of the holder. The pockets permit the lenses to be removably positioned therein either after or, preferably before the lens holder is introduced into the eye. For example, the lens holder may be in the form of a disk with lens pockets shaped so as to secure the lenses in a coplanar relationship with the longitudinal axis of the disk. In a preferred embodiment of the invention, such a holder is used to secure a multiaperture array of lenses adjacent to the irial opening. However, as used herein the securing means are also intended to include a flexible holder which integrally incorporates a plurality of lens bodies. For example, both the holder and the lenses may be formed from a single body of polymeric material, as by milling, injection molding or a like process.

When all of the lenses introduced into the lens pockets have the same focal length, they will function together in the manner of a superimposition eye. Each individual lens will form an image of its own. The lenses can be arranged, and the holder positioned, so that all the images are superimposed on the retina to form a common image for a given field of view.

The advantage of the use of a multiaperture lens array in the present intraocular lens structure is that the individual lenses employed can be considerably smaller than the artificial lens bodies heretofore employed to replace the natural lens in intraocular implant operations. Therefore, according to the practice of the present invention, a plurality of lens bodies can be secured in a flexible lens holder to form a flexible intraocular multiaperture structure which may be rolled, folded or otherwise compressed and inserted into the interior of the eye through an incision of smaller size than heretofore required to introduce a single aperture lens. Once within the interior of the eye, the holder is decompressed and secured to the appropriate interior structure of the eye so as to securely position the lenses adjacent to, and in a substantially coplanar fashion with the plane of the irial opening.

The lens holder of the present invention may also be used to introduce two or more lenses of differing focal length into the eye, so as to produce bifocal or trifocal vision correction.

Preferably the disk-shaped lens holder of the present invention will have its outermost circumferential volume in the shape of a spherical or oblong toroid body (torus). The torus will have at least one lens insert slit which is preferably aligned along a chord of the circumference of the torus, and which communicates between the exterior and interior circumferential surfaces of the torus. The interior of the torus will be partially or completely spanned by a flexible membrane. The membrane is shaped so as to define one or more lens pockets and one or more lens slide passages. Each lens slide passageway communicates between a lens pocket and an insert slit. Each slit, passageway and pocket system are sized so as to admit an artificial lens and to bring the lens into coplanar alignment with the membrane. During lens admission, the lens will be moved from the exterior of the torus, through the slit and the passageway and into the interior of the pocket, where it will be secured therein by the opposed compressive forces of the upper and lower pocket walls. The pocket walls will be formed of a transparent plastic film.

In use, one or preferably two or more lenses may be inserted into the holder before it is inserted into the eye. The flexible holder will then be folded or rolled into a thin cylinder and inserted through the corneal incision into the anterior chamber of the eye. The holder will then be unrolled and moved into its final position within the eye. Alternatively, one or more lenses may be inserted into the holder after it has been introduced into the interior of the eye. A preferred embodiment of the present flexible lens holder further comprises means whereby its flexibility may be reduced after the lens holder has been positioned in the eye, thus reducing the possibility of irritation or other damage due to localized pressure and securing the lens structure against rotation or other loss of position.

In this embodiment, the toroid body further defines a continuous interior channel which penetrates a major portion of the circumference of the body, and is sized so as to admit a resilient stiffening filament, which functions to reduce the flexibility of the holder. The filament will preferably be fed into the channel via a feeder hose which is cojoined to the channel at one end. The stiffening filament is then inserted into the toric channel by way of the feeder hose, which has been positioned so as to extend through the corneal incision to the outside of the eye. After the filament has been introduced into the channel, the hose and the excess filament may be clipped off, leaving the intraocular lens structure securely positioned within the eye.

DETAILED DESCRIPTION OF THE INVENTION

Figure 1:
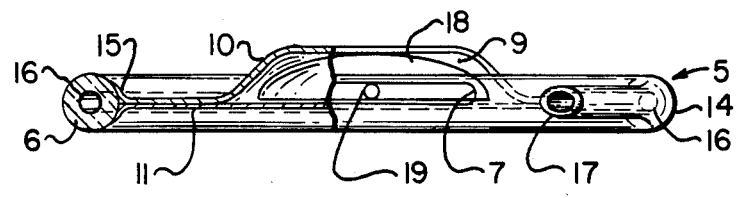
FIG. 1 is a edge-wise, partially cut-away view of one preferred embodiment of a lens holder 5 of the present invention.
Figure 2:
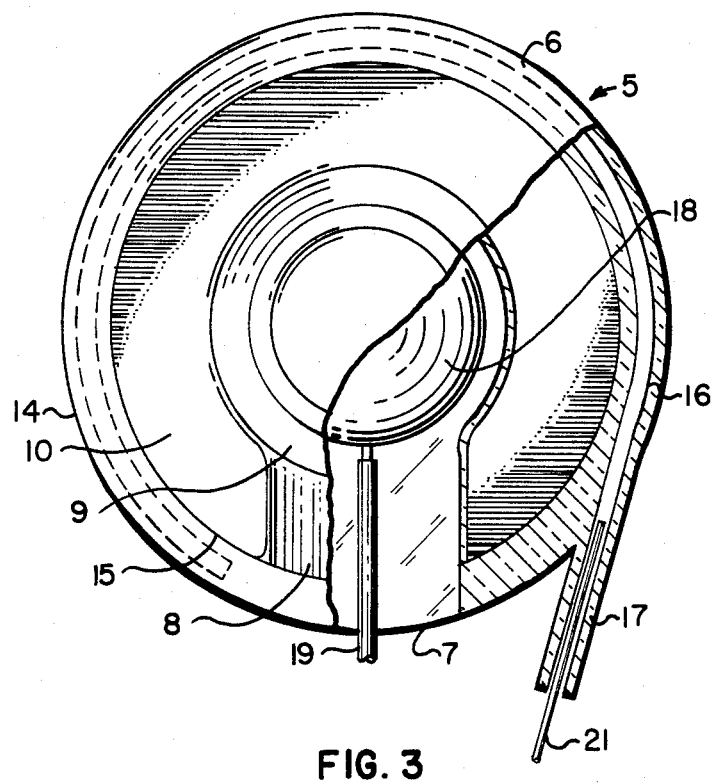
FIG. 2 is a frontal view of the lens holder of FIG. 1, viewed through a partial horizontal section.

Referring now to the figures in greater detail, it can be seen that lens holder 5 has a generally circular outer toroid body (torus) 6 which defines an oblong lens insert slit 7. Slit 7 completely penetrates the flexible body of the torus communicating between an outer circumferential surface 14 and an inner circumferential surface 15 of the torus. The inner opening of the slit 7 communicates with lens slide passageway 8 which itself communicates with one or more lens pockets 9. The outer edges of lens slide 8 and lens pocket 9 are preferably defined by the bonded lower and upper surfaces, respectively of an upper film 10 and a lower film 11, respectively. The films are superimposed and extend across the torus so as to completely fill the area defined by the inner circumferential surface 15 of torus 6. The outer edges of said films are coincident with the inner circumferential surface 15 of torus 6 and are joined thereto. As is the torus, both films will be formed of a flexible polymeric material which preferably will be substantially transparent throughout, and which must be optically transparent within the area of lens pocket 9. Except within the voids of the lens slide 8 and the lens pocket 9, the two films will be integrally bonded together throughout the inner circumferential area of the torus into a single membrane. The films may be bonded to each other and to the inner torus surface 15 by means of a transparent adhesive, by thermal techniques or by a combination thereof. Alternatively, the lens pocket and the lens slide passageway may be formed within the body of a single membrane, e.g. by suitable molding techniques. The non-bonded areas of the membrane or of films 10 and 11 define the upper and lower surfaces of lens pocket or pockets 9. Each pocket is flexible and is designed to deform slightly so as to secure lens 18 in a coplanar fashion with the membrane or films by means of the opposed compressive forces of the upper and lower pocket surfaces. Since torus 6 will also be formed from a flexible material, the area of the entrance slit 7 may be sized so as to be slightly less than the vertical area of lens 18, since the walls of slit 7 will deform slightly so as to admit the lens into pocket 9.

Torus 6 will preferably also have attached thereto feeder hose 17 which communicates with a continuous channel 16. Channel 16 preferably is substantially centered within the body of the torus and penetrates a major portion of the circumference thereof. Stiffening filament 21 may be introduced into torus channel 16 via feeder hose 17 where it acts to increase the rigidity of holder 5 after it has been positioned within the anterior scleral cleft, posterior capsule, or ciliary sulcus of the eye.

Figure 5:
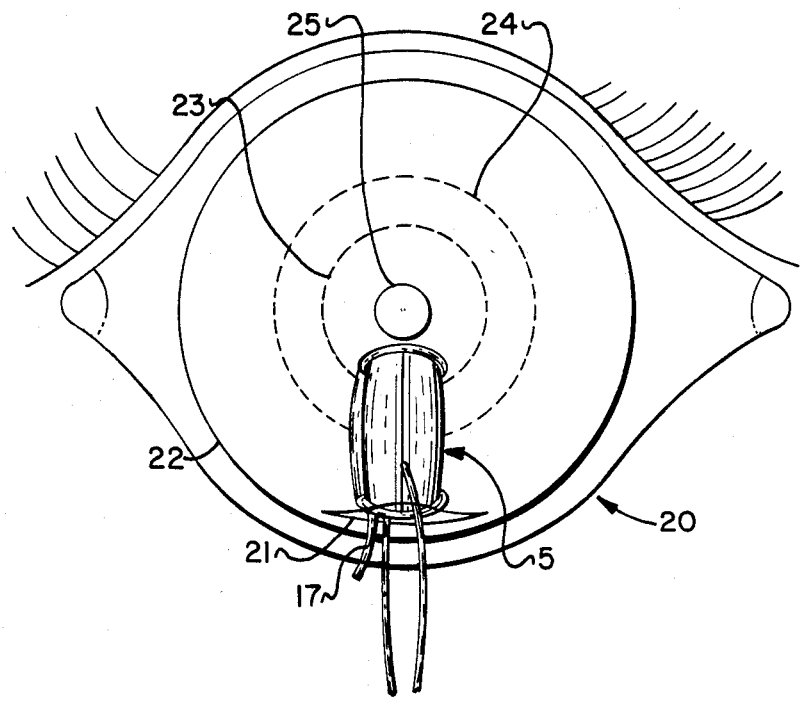
FIG. 5 is a diagrammatic frontal view of the eye illustrating the insertion of the holder of FIG. 3 into the interior thereof, as during a lens replacement operation.
Figure 4:
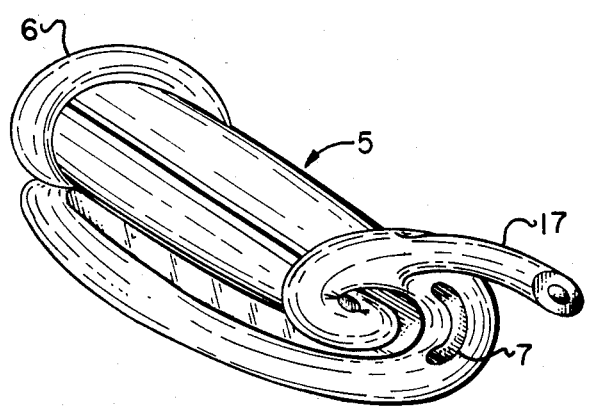
FIG. 4 is a perspective plan view of the lens holder of FIG. 3 which has been compressed into a roll.

In use, lens holder 5, prior to the introduction of lens 18 or filament 21, is tightly compressed as shown in FIG. 4, i.e. by rolling or folding, into a cylindrical body. As shown in FIG. 5, compressed holder 5 is then longitudinally inserted into the anterior chamber of the eye 20 through an appropriately positioned and sized incision 21, e.g. in the lower portion of the cornea 22. Feeder hose 17 will exit the eye via the incision. Once inserted into the anterior chamber, the holder is unrolled and the lenses 18 are positioned individually in the lens pockets 9. Preferably, each lens will be introduced into the pocket 9 through opening 7 and slide 8 by means of an attached rigid or semiflexible insertion rod 19. Preferably, rod 19 will be releasably attached at or adjacent to the edge of lens 18. After lens 18 is positioned satisfactorily within pocket 9, the rod is detached from the lens, e.g. by unscrewing it or by snapping or twisting it off, and is withdrawn from the holder and the eye.

Lens holder 5 is then moved into its final position within the chamber of the eye. Preferably, holder 5 is positioned in front of the pupil 23 and seated in the groove located between the scleral spur and the iris 25 (the anterior chamber wedge 24).

Although the diameter of the present lens holders will necessarily vary according to the internal measurements of the eyes to which they will be fitted, generally useful diameters for this embodiment of the present holder will be about 10–15 mm, preferably about 12–13 mm.

The present holders will preferably be sized so as to fit snugly into this natural groove without exerting undue pressure thereon. However, the high flexibility of the present holders renders it highly desirable to increase the rigidity of the torus after the holder has been positioned in order to reduce the possibility that the holder will rotate, shift or otherwise lose its original position. To accomplish this stiffening, a flexible filament 21 is introduced into the circumferential torus channel 16 via feeder hose 17. The filament is preferably formed of a hard, flexible material such as wire or hard plastic. After a length of filament 17 adequate to substantially fill channel 16 has been introduced therein, the excess filament and the feeder hose 17 may be cut off and removed from the eye. The clipped edge of the stiffening filament may be secured within the toroid body simply by pressing it into the interior of the channel wall. Alternatively, the entire holder may be formed of a suitable thermoplastic polymer and inserted and positioned in the eye at a temperature at which its flexibility is substantially higher than at body temperature. Upon cooling to body temperature, the holder will rigidify and self-lock in the desired position. The incision is then sutured.

The intraocular insertion and fixation of the present lens holder and lenses in this manner offers a number of advantages not heretofore realized by intraocular lens structures. In the first place, the lens holder can be formed entirely from a flexible, inert polymer such as a silicone rubber, polytetrafluoroethylene or polyhydroxymethacrylate. The high flexibility imparted to the holder permits it to be compressed, e.g. by rolling, into a cylindrical body having a lateral cross-section which is narrower than the later-introduced lens. Therefore, the corneal incision, which must normally be 8–9 mm in length in order to accommodate the lens and its associated connective appendages, now need be no longer than the lens width, as measured perpendicularly to the optical axis of the lens. The incision required to introduce will commonly be no more than about 3–4 mm in length.

In the second place, the incorporation of multiple lens pockets into the present lens holders permits the substitution of multiaperture optical array for the single lens. When employed in this fashion, the present lens holders can incorporate two or more lenses of substantially identical focal length.

Although the resolving power of a lens is reduced linearly as the lens diameter is reduced, the volume of the lens decreases with the third power of the lens diameter. The resolving power of the human eye is determined by the size of the retinal cones and the distance between then. The natural lens has evolved to match this resolving power. However, the sensitivity of the cones deteriorates with age so that the inherent resolving power of the eye's lens is no longer fully utilized. In such situations, an array of small-diameter lenses may not appreciably deteriorate the patient's seeing potential. However, the use of two or more, preferably about 2–5 small lenses allows an easier and less risky implant procedure. In procedures in which the lenses are introduced into the holder after the holder has been inserted into the eye, the reduced lens diameter permits a concommitant reduction in the minimum length of the incision from the minimum required for the insertion of a single lens.

The reduction in individual lens diameter when two or more lenses are employed also allows the lenses to be incorporated into the holder, e.g. placed within the lens pockets, prior to the insertion of the holder into the eye. This is possible since the smaller lenses can be rolled or folded up with the holder without substantially increasing the minimal transverse width of the compressed holder over than attainable with a lens-free holder. The reduction of the lens insertion step, which normally must be carried out after the holder has been inserted into the eye and allowed to assume its original shape, is highly preferred since it greatly reduces the total time required for the lens replacement operation and thus reduces the patient's trauma and risk of damage to the eye.

Finally, the decompression of the soft, flexible holders of the present invention is not accompanied by the risk of cutting or tearing the eye which accompanies the intraocular decompression of the rigid, springy feet or loops commonly employed to position and secure the lens body within the eye. Furthermore, the introduction of the stiffening filament into the toric body allows the even, incremental increase of radial pressure which acts to secure the holder within the anterior ridge or the capsular sac, thus effectively positioning the lens or lens array adjacent to the pupil. Thus the present holders readily adjust to normal distortions of the eye while remaining firmly positioned.

Figure 3:
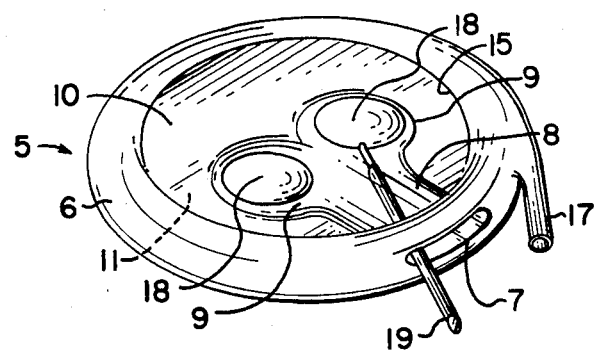
FIG. 3 is a perspective plan view of a lens holder similar to that depicted in FIGS. 1 and 2, differing only in that it is designed to support two intraocular lenses within the eye.

However, it is also within the scope of the present invention to employ flexible lens holders of a diameter smaller than that required to directly contact the outer edge of the holder with an internal eye structure. For example the diameter of the flexible lens holder of FIG. 3 could be reduced to within the size range of commonly-employed artificial lens bodies, e.g. about 4–6 mm. Two lenses, each about 2–3 mm in diameter, could be incorporated into the body of the holder, the holder folded and inserted into the interior of the eye. Such a holder would be secured within the eye by means commonly employed to secure hard artificial lens bodies. Such means could include pre-attached feet or flexible loops such as those disclosed in the patents cited hereinabove.

Although the invention has been described by reference to certain preferred embodiments, those of skill in the art will recognize that many modifications may be made therein without departing from the spirit and scope of the invention.

What is claimed is:

1. An intraocular lens structure useful to position and secure a plurality of artificial lenses in the interior of a human eye and insertable through an incision in said eye, said lens structure comprising a flexible lens holder incorporating means to affix said holder within the interior of the eye, and said lens holder comprising means adapted to individually secure said lenses in a coplanar relationship adjacent to the irial opening of said eye.

2. The intraocular lens structure of claim 1 wherein said holder comprises at least two optically transparent pockets, said pockets incorporating artificial lenses of the same focal length.

3. The intraocular lens structure of claim 1 wherein said holder comprises at least two pockets, said pockets incorporating lenses of differing focal lengths.

4. The intraocular lens structure of claim 1 wherein the holder comprises a disk of flexible polymeric material.

5. The intraocular lens structure of claim 4 wherein said lens holder comprises a flexible toroid body and a flexible membrane extending across said toroid body and having an outer edge coincident with the inner circumferential surface of said toroid body and being joined thereto, said membrane defining a plurality of transparent lens pockets, said pockets being sized so as to admit an artificial lens into each pocket and to bring said lens into coplanar alignment with said membrane.

6. An intraocular lens holder useful to position and secure an artificial lens in the interior of a human eye and insertable through an incision in said eye, said lens holder comprising:
(a) a flexible toroid body defining a lens insert slit, said slit communicating between an outer circumferential surface of the toroid body and an inner circumferential surface of said body; and
(b) a flexible membrane extending across said toroid body and having an outer edge coincident with said inner circumferential surface of said toroid body and being joined thereto, said membrane defining a transparent lens pocket and a lens slide passageway communicating between said pocket and said insert slit, wherein said slit, said passageway and said pocket are sized so as to admit an artificial lens and to bring said lens into coplanar alignment with said membrane.

7. The intraocular lens holder of claim 6 wherein said toroid body defines a continuous interior channel which penetrates a major portion of said toroid body.

8. The intraocular lens holder of claim 6 which further comprises a feeder hose one end of which communicates with said channel.

9. The intraocular lens holder of claim 8 wherein the channel encompasses a resilient stiffening filament which is introduced into said channel by way of said hose and substantially reduces the flexibility of said toroid body.

10. The intraocular lens holder of claim 6 wherein the edges of said pocket and said slide passageway are defined by the bonded upper surface of a lower film and the lower surface of an upper film which are superimposed and bonded together so as to form said flexible membrane.

11. The intraocular lens holder of claim 10 wherein the lens pocket incorporates an artificial lens which is secured therein by means of the opposed compressive forces of the upper and lower pocket surfaces.

12. The intraocular lens holder of claim 11 wherein an inserting rod is removably attached to said lens.

13. The intraocular lens holder of claim 6 wherein the lens slide passageway communicates with a plurality of lens pockets.

14. The intraocular lens holder of claim 13 wherein said toric body and said membrane are formed from an inert polymeric material.

15. The intraocular lens holder of claim 14 wherein said toric body and said membrane are formed from silicone rubber.

16. An intraocular lens holder useful to position and secure an artificial lens in the interior of a human eye and insertable through an incision in said eye, said lens holder comprising:
(a) a flexible toroid body defining a continuous interior channel which penetrates a major portion of said toroid body, said body also defining a lens insert slit, said slit communicating between an outer circumferential surface of said toroid body and an inner circumferential surface of said body, the long axis of said slit coinciding with a chord of the circumference of said toroid body;
(b) a flexible membrane extending across said toroid body and having an outer edge coincident with an inner circumferential surface of said toroid body and being joined thereto, said membrane defining a plurality of transparent lens pockets and a lens slide passageway communicating between said pockets and said insert slit, wherein said slit, said passageway and each said pocket are sized so as to admit an artificial lens and to bring said lens into coplanar alignment with said membrane;
(c) a feed opening communicating with said channel; and
(d) a resilient stiffening filament constructed and arranged to be inserted through said feed opening into said channel after the lens holder is located within the eye to substantially reduce the flexibility of said toroid body.

17. A method for implanting, through an incision in the cornea of the eye, a plurality of artificial lenses within a human eye from which the natural lens has been removed, which utilizes a flexible lens holder incorporating means to securely position said holder within the interior of said eye, said lens holder comprising means adapted to secure said artificial lenses in a coplanar relationship adjacent to the irial opening of the eye, comprising the steps of:
(a) individually securing a plurality of artificial lenses to said holder;
(b) compressing said lens holder into a folded body having a longitudinal axis;
(c) inserting the compressed lens holder longitudinally through the incision into the anterior chamber of the eye;
(d) unfolding said lens holder; and
(e) securely positioning said holder adjacent to the irial opening so that horizontal plane of said lenses is substantially adjacent and parallel to the plane of the irial opening.

18. The method of claim 17 wherein the flexible lens holder comprises a disk of flexible polymeric material which is positioned within the eye so that the outer circumferential edge of said holder abuts the anterior chamber wedge.

19. The method of claim 17 wherein said artificial lenses are of equal focal length.

20. The method of claim 17 wherein said artificial lenses are of differing focal lengths.

21. A method for implanting, through an incision in the cornea of the eye, an artificial lens within a human eye from which the natural lens has been removed, which utilizes a lens holder having a flexible toroid body of predetermined diameter, defining a lens insert slit, said slit communicating between an outer circumferential surface of the toroid body and an inner circumferential surface of said body, and a flexible membrane extending across said toroid body and having an outer edge coincident with said inner circumferential surface of said toroid body and being joined thereto, said membrane defining a transparent lens pocket and a lens slide passageway communicating between said pocket and said insert slit, wherein said slit, said passageway and said pocket are sized so as to admit an artificial lens and to bring said lens into coplanar alignment with said membrane, comprising the steps of:
   (a) compressing said lens holder into a generally cylindrical body having a longitudinal axis;
   (b) inserting the compressed lens holder longitudinally through the incision into the anterior chamber of the eye;
   (c) decompressing said lens holder and inserting a synthetic lens into the lens pocket through the lens insert slit and the lens slide passageway; and
   (d) positioning said holder so that the outer circumferential surface of said holder abuts the anterior chamber wedge so as to substantially center said lens in front of the pupil.

22. The method of claim 21 wherein, after step (c), the flexibility of the lens is substantially reduced by introducing a resilient stiffening filament into an interior channel which penetrates a major portion of the toroid body of the lens holder.

23. The method of claim 21 wherein the lens slide of the lens holder communicates with a plurality of lens pockets, said method further comprising individually introducing a plurality of artificial lenses into said pockets after step (b).

24. The method of claim 23 wherein said lenses are inserted into said pockets by means of individual inserting rods attached at or adjacent to the lens edge.

25. The method of claim 21 wherein the lens slide of the lens holder communicates with a plurality of lens pockets, said method further comprising individually introducing a plurality of artificial lenses into said pockets prior to step (a).

26. An intraocular lens structure useful to position and secure a plurality of artificial lenses in the interior of a human eye and insertable through an incision in said eye, said lens structure comprising a flexible lens holder incorporating means to affix said holder within the interior of the eye, and said lens holder integrally incorporating a plurality of artificial lenses which are in a coplanar relationship adjacent to the irial opening of said eye when said holder is affixed within the eye.

27. The lens structure of claim 26 wherein the lens holder and the lenses are formed from a single body of polymeric material.

28. The lens structure of claim 26 wherein the lenses are of same focus length.

29. The lens structure of claim 26 wherein the lenses are of differing focal lengths.

* * * * *